(12) United States Patent
Scott, II et al.

(10) Patent No.: US 11,947,437 B2
(45) Date of Patent: Apr. 2, 2024

(54) ASSIGNMENT OF ROBOTIC DEVICES USING PREDICTIVE ANALYTICS

(71) Applicant: International Business Machines Corporation, Armonk, NY (US)

(72) Inventors: Willie L. Scott, II, Austin, TX (US); Charu Pandhi, Round Rock, TX (US); Seema Nagar, Bangalore (IN); Kuntal Dey, New Delhi (IN)

(73) Assignee: International Business Machines Corporation, Armonk, NY (US)

( * ) Notice: Subject to any disclaimer, the term of this patent is extended or adjusted under 35 U.S.C. 154(b) by 917 days.

(21) Appl. No.: 16/942,071

(22) Filed: Jul. 29, 2020

(65) Prior Publication Data

US 2022/0035727 A1 Feb. 3, 2022

(51) Int. Cl.
*B25J 11/00* (2006.01)
*B25J 9/00* (2006.01)
(Continued)

(52) U.S. Cl.
CPC ......... *G06F 11/3438* (2013.01); *B25J 9/0084* (2013.01); *G06F 9/5011* (2013.01);
(Continued)

(58) Field of Classification Search
CPC ...... B25J 11/009; B25J 9/0084; B25J 9/1661; G05B 19/41865; G06F 11/3438; G06N 20/00; G16H 10/60; G16H 40/40
See application file for complete search history.

(56) References Cited

U.S. PATENT DOCUMENTS

| 10,311,388 B2 | 6/2019 | Olsen et al. |
| 2011/0264482 A1 | 10/2011 | Rahmouni et al. |

(Continued)

FOREIGN PATENT DOCUMENTS

| CN | 105835069 A | 8/2016 |
| EP | 3588290 A1 | 1/2020 |

(Continued)

OTHER PUBLICATIONS

Breazeal, C., "Designing social robots for older adults—MIT Media Lab," https://www.media.mit.edu/articles/designing-social-robots-for-older-adults/, printed Feb. 14, 2020, 5 pgs.
(Continued)

*Primary Examiner* — Jaime Figueroa
*Assistant Examiner* — Zachary Joseph Wallace
(74) *Attorney, Agent, or Firm* — Peter Suchecki

(57) ABSTRACT

Provided is a method, computer program product, and system for automatically assigning robotic devices to users based on need using predictive analytics. A processor may monitor activities performed by one or more users. The processor may determine, based on the monitoring, a set of activities that require assistance from a robotic device when being performed by the one or more users. The processor may match the set of activities to a set of capabilities related to a plurality of robotic devices. The processor may identify, based on the matching, a first robotic device that is capable of assisting the one or more users in performing a first activity of the set of activities. The processor may deploy the first robotic device to assist the one or more users in performing the first activity.

17 Claims, 8 Drawing Sheets

(51) Int. Cl.
G06F 9/50 (2006.01)
G06F 11/34 (2006.01)
G06N 20/00 (2019.01)
G16H 10/60 (2018.01)
G16H 40/63 (2018.01)

(52) U.S. Cl.
CPC ............ *G06N 20/00* (2019.01); *G16H 10/60* (2018.01); *G16H 40/63* (2018.01); *B25J 11/009* (2013.01)

(56) References Cited

U.S. PATENT DOCUMENTS

| | | | |
|---|---|---|---|
| 2014/0067729 A1 | 3/2014 | Kozloski et al. | |
| 2014/0350725 A1 | 11/2014 | Lafary et al. | |
| 2014/0365258 A1 | 12/2014 | Vestal et al. | |
| 2016/0217266 A1 | 7/2016 | Damani et al. | |
| 2018/0102190 A1 | 4/2018 | Hogue et al. | |
| 2018/0253662 A1 | 9/2018 | Booch et al. | |
| 2020/0214626 A1* | 7/2020 | Boyle | A61B 5/6896 |
| 2021/0373576 A1* | 12/2021 | Sohn | B25J 9/1697 |

FOREIGN PATENT DOCUMENTS

| | | |
|---|---|---|
| KR | 20110103446 A | 9/2011 |
| KR | 101960835 B1 | 3/2019 |
| WO | 2013054257 A1 | 4/2013 |
| WO | 2019046602 A1 | 3/2019 |

OTHER PUBLICATIONS

Calì et al., "Logic-Based Approach for Matching User Profiles." In: M. Negoita et al. (eds), Knowledge-Based Intelligent Information and Engineering Systems. KES 2004, Lecture Notes in Computer Science, vol. 3215. pp. 187-195, 2004, Springer.

Credence Research, "Medical Robotics Market to Reach Over US$ 20 Bn by 2023," https://www.credenceresearch.com/press/global-medical-robotics-market, printed Feb. 14, 2020, 2 pgs.

Geeks for Geeks, "Maximum Bipartitie Matching—GeeksforGeeks," https://www.geeksforgeeks.org/maximum-pipartite-matching/, printed Feb. 14, 2020, 5 pgs.

Ghassemi et al., "Decentralized Task Allocation in Multi-Robot Systems via Bipartite Graph Matching Augmented with Fuzzy Clustering." (Submitted on Jul. 20, 2018), https://arxiv.org/abs/1807.07957.

IBM, "Robot Schedule," https://www-356.IBM.com/partnerworld/gsd/solutiondetails.do?solution=18097&lc=en&stateCd=P&tab=2, printed Feb. 14, 2020, 1 pg.

Mell et al., "The NIST Definition of Cloud Computing," Recommendations of the National Institute of Standards and Technology, U.S. Department of Commerce, Special Publication 800-145, Sep. 2011, 7 pgs.

Meola, A., "Future Demand for Elderly Care Services Like Assisted Living & In-Home Care are Rife for Digital Disruption," https://www.businessinsider.com/senior-care-market-trends, Jul. 8, 2019, printed Feb. 14, 2020, 5 pgs.

Motion Control Robotics, "Robot Inertia vs. Payload," https://motioncontrolsrobotics.com/robot-inertia-vs-payload/, printed Feb. 14, 2020, 5 pgs.

Peng, R., "Bipartite Matching," https://www.cc.gatech.edu/%7Erpeng/CS3510_F17/Notes/Nov1BipartiteMatching.pdf, CS 3510 Design & Analysis of Algorithms, Section A, Lecture #16, Nov. 1, 2017, 4 pgs.

Roche, "This is personalised healthcare," https://www.roche.com/about/priorities/personalised_healthcare.htm, printed Feb. 14, 2020, 11 pgs.

Senior Care, "What is Elder Care," https://www.seniorcare.org/elder-care/, printed Feb. 14, 2020, 2 pgs.

Wikipedia, "Bipartite graph," https://en.wikipedia.org/wiki/Bipartite_graph, printed Feb. 14, 2020, 7 pgs.

Zhu et al., "Crane Scheduling with Spatial Constraints: Mathematical Model and Solving Approaches," Naval Research Logistics, vol. 51, pp. 386-406, 2004.

\* cited by examiner

ASSIGNMENT OF ROBOTIC DEVICES USING PREDICTIVE ANALYTICS

BACKGROUND

The present disclosure relates generally to the field of robotic devices, and more specifically to automatically assigning robotic devices to users based on need using predictive analytics.

The use of robotic devices to help perform various tasks has become prevalent across many industries. Industries have increased the implementation of robotic devices for performance reasons, such as increased precision, limited errors, faster operation, and significant reliability when performing tasks. Specifically, the healthcare industry has utilized robotic devices to assist in performing activities such as surgeries, patient rehabilitation, medical transportation, medication dispensing, social interaction, and biohazard maintenance.

SUMMARY

Embodiments of the present disclosure include a method, computer program product, and system for automatically assigning robotic devices to users based on need using predictive analytics. A processor may monitor activities performed by one or more users. The processor may determine, based on the monitoring, a set of activities that require assistance from a robotic device when being performed by the one or more users. The processor may match the set of activities to a set of capabilities related to a plurality of robotic devices. The processor may identify, based on the matching, a first robotic device that is capable of assisting the one or more users in performing a first activity of the set of activities. The processor may deploy the first robotic device to assist the one or more users in performing the first activity.

The above summary is not intended to describe each illustrated embodiment or every implementation of the present disclosure.

BRIEF DESCRIPTION OF THE DRAWINGS

The drawings included in the present disclosure are incorporated into, and form part of, the specification. They illustrate embodiments of the present disclosure and, along with the description, serve to explain the principles of the disclosure. The drawings are only illustrative of typical embodiments and do not limit the disclosure.

Figure 1:
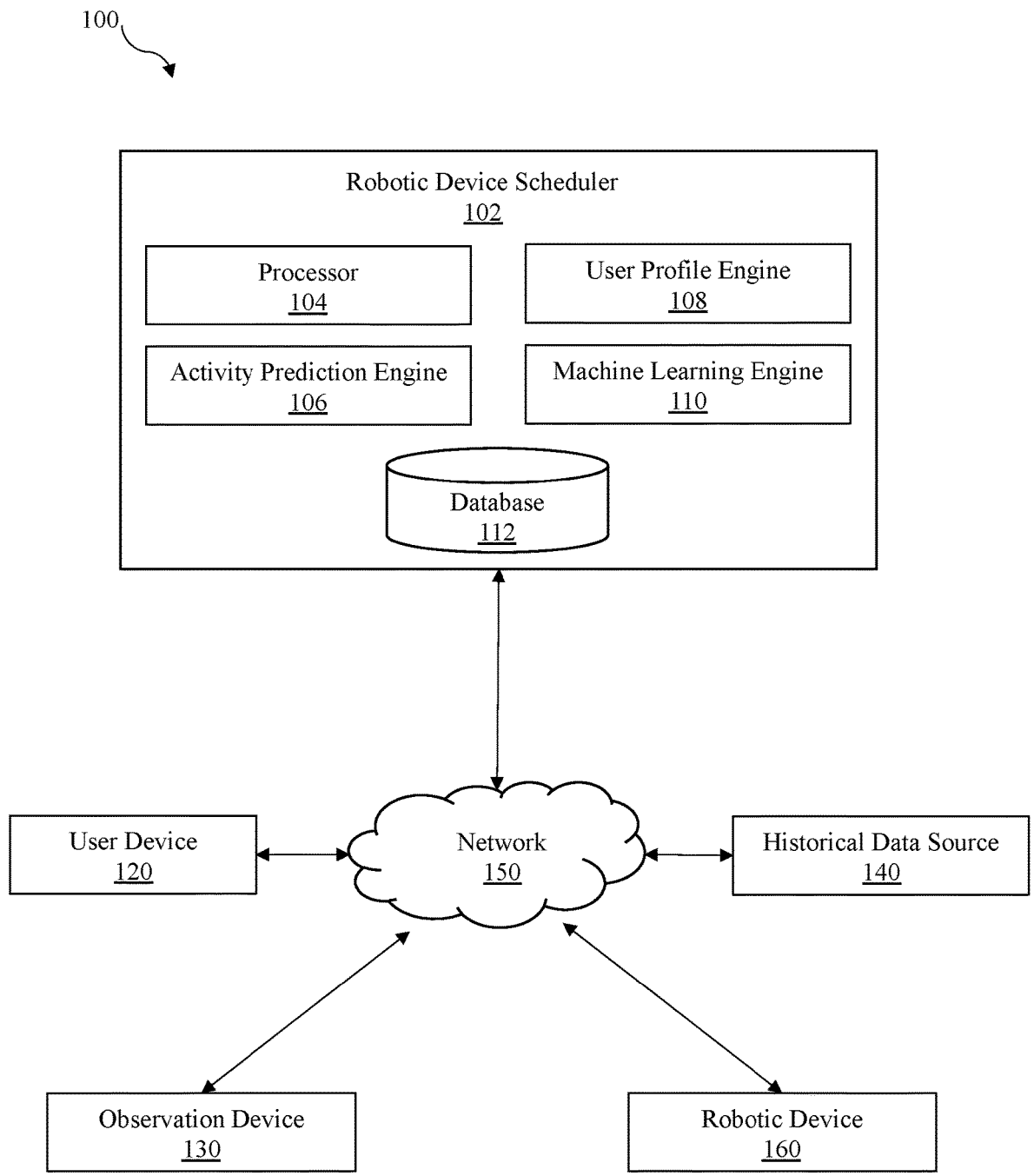
FIG. 1 illustrates a block diagram of a robotic device assignment system, in accordance with embodiments of the present disclosure.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the disclosure.

DETAILED DESCRIPTION

Aspects of the present disclosure relate to the field of robotic devices, and more particularly to dynamically assigning robotic devices to users based on need using predictive analytics. While the present disclosure is not necessarily limited to such applications, various aspects of the disclosure may be appreciated through a discussion of various examples using this context.

The use of robotic devices to help perform various tasks has become prevalent across many industries. Specifically, the healthcare industry has utilized robotic devices to assist in performing various activities such as surgeries, patient rehabilitation, medical transportation, medication dispensing, social interaction, and biohazard maintenance.

Healthcare robotic devices, such as caretaker robots, rehabilitation robots, social robots, medication dispensing robots, and the like may be used to provide specialized care to patients based on specific medical and healthcare needs. These medical and healthcare needs may vary based on the environment where the robotic devices are utilized. For example, robotic devices used in a rehabilitation healthcare center may be used to aid patients in performing various rehabilitation exercises such as walking, moving extremities, stretching, etc. Meanwhile robotic devices deployed in an assisted living facility may be utilized to aid healthcare workers in performing various day to day tasks such as lifting patients/residents, performing sanitary activities, providing medications, and/or participating in social interactions.

In many instances, each robotic device deployed in the specific environment will not be capable of performing and/or assisting in all types of activities required for a given patient. For example, a rehabilitation robot may not be able to perform similar tasks as a medication dispensing robot and/or a social interaction robot. Therefore, multiple robotic devices having various capabilities may be needed to perform a set of activities for each patient depending on specific needs.

Given a plurality of patients and desired patient care activities requiring robotic device assistance, it is imperative that each patient is assigned a suitable robot or robots based on what current activity the patient needs assistance in performing at any given time. As the need for robotic devices increases among the plurality of patients, the availability of the robotic devices for aiding in performing specific tasks may be inefficiently determined by manual scheduling. This challenge may increase over time as manual and/or static allocation can be unwieldy, as the scheduling of required patient activities may change with time due to ever changing healthcare needs.

Embodiments of the present disclosure relate to a method, computer program product, and system for dynamically assigning robotic devices to users (e.g., patients, residents, etc.) based on need at any given time. The system may determine a set of activities that require assistance of a robotic device by monitoring/observing users performing actions over a period of time. The system then allocates appropriate robotic devices based on capabilities to assist users in performing respective activities at predicted times in an automated way. As activities are completed by each user with the aid of one or more robotic devices, the system dynamically adjusts the allocation of all robotic devices based on the predicted next activity and availability of a required robotic device. In this way, the present disclosure provides personalized care to each user at a granular level based on the given activity and the type of assistance required for completing each activity by dynamically assigning robotic devices to users on a continuous basis while reducing inefficiencies in utilizing each robotic device's capabilities and runtime.

In embodiments, the system may monitor activities performed by one or more users using one or more observation devices. For example, the system may monitor activities by collecting observation data from a set of Internet of Things (IoT) cameras and/or wearable health monitoring sensors (e.g., smart band, smart watch, smart sensor, etc.) that have been used to observe/monitor a user performing various activities. For example, the system may monitor patients at a healthcare facility performing various activities, such as physical therapy movements, taking medications, walking, eating, etc. The system may collect observation data related to these activities over a period of time (e.g., 1 day, 1 week, 1 month, etc.) to determine a pattern of activities performed by the patients.

In embodiments, the system uses the observation data to determine and/or predict a set of activities that require assistance from one or more robotic devices when being performed by the users. The system may identify the set of activities by using an activity prediction engine that utilizes various recognition techniques (e.g., image recognition, facial recognition, biometric monitoring, etc.) to determine which activities require assistance of a robotic device. For example, the system may identify that a first user may need assistance when walking based on image data indicating the first user is having difficulty balancing due to a leg impairment. In another example, the system may identify that a second user needs assistance moving their arm based on image data of the second user performing physical therapy with assistance from a physical therapist. In another example, the system may identify through both biometric monitoring and image data that any time a user's blood pressure is elevated, the user is provided with blood pressure medication by another user (e.g., a doctor or nurse).

In embodiments, when determining the set of activities requiring assistance from one or more robotic devices, the system may supplement the observation data by collecting and analyzing various information from historical data sources related to each of the users. For example, the system may analyze electronic health records (EHR) of a patient to determine various impairments that may require the assistance of a robotic device. For example, EHR may indicate a user requires various medications, has a leg or arm impairment, and/or requires assistance when performing certain activities such as walking, maintaining balance, eating, etc. In embodiments, the system may utilize known techniques to analyze the EHR (e.g., natural language understanding (NLU), natural language processing (NLP), image recognition, etc.) to make activity determinations. Using the historical data source information in conjunction with the observation data, the system can improve the prediction of activities requiring assistance of robotic devices for each of the users.

In embodiments, metadata information associated with the observation data may be used by the system to determine a time period, location, and/or schedule for each predicted activity that requires assistance of the robotic device. For example, while monitoring the users, the system may determine that a first user needs assistance walking at a first time period and assistance getting into bed at a second time period, while a second user needs assistance reading at a first time period and assistance receiving medication at a second time period. The determined time periods related to each activity may be utilized by the system to predict when and what type of robotic device is needed for each activity.

In embodiments, once the set of activities requiring assistance from one or more robotic devices is determined, the system will match the set of activities for each user with a set of capabilities related to one or more robotic devices from a plurality of robotic devices. Returning to the previous example, the system will match a first robotic device capable of assisting with walking and a second robotic device capable of lifting to the first user, while a third robotic device capable of assisting with reading and a fourth robotic device capable of dispensing medication may be assigned to the second user. In embodiments, some capabilities of the robotic devices may overlap allowing a respective robotic device to be assigned to perform more than one activity for the same user (e.g., a robotic device capable of both assisting with walking and lifting a user).

In embodiments, the system will identify the set of capabilities for each of the one or more robotic devices from an enumeration of possible care capabilities stored in a database and/or listing of available robotic device. The enumeration of care capabilities may include capabilities such as a payload (e.g., weight that the robotic device can lift), physical activities the robotic device can perform (e.g., physical therapy motions, feeding assistance, medication dispensing, biometric monitoring, etc.), generation/age of the robotic device, robotic inertia, the version of software operating system and/or firmware running on the robotic device, etc.

In embodiments, the system may match the users with robotic devices that are capable of performing the set of activities by generating a bipartite graph using a bipartite graph matching algorithm. The bipartite graph may include a set of user nodes associated with the set of activities to be performed and a set of robotic device nodes associated with the set of capabilities related to each robotic device. In embodiments, the system may score each capability of the set of capabilities based on a suitability of the robotic device's ability to perform the given activity from the set of activities. The score may be determined by using any type of machine learning and/or scoring model. The score may be any type of value (e.g., range from 0 to 1, percentage out of 100, etc.) used to rate the capability of each robotic device in performing the given activity. For example, the system may give a robotic device that is capable of lifting a user a score of 1 for an activity related to lifting and a score of 0 for an activity related to providing medication. In embodiments, the score may be continuously adjusted based on an analysis of the current capabilities of the robotic devices. For example, the robotic devices may be upgraded over time regarding their capabilities (e.g., software upgrades, addition of new parts, new generation of robot, etc.) which may result in adjusted/higher scores.

In some embodiments, the system may include weighted scores for various capabilities depending on the importance of the capability in relation to the respective environment utilizing the robotic device. For example, robotic devices that are capable of assisting range of motion exercises and/or helping a user walk may be provided weighted scores in a rehabilitation environment over a robotic device that is used to only provide medication. Alternatively, in a hospital setting where users may urgently require medications on strict time schedules, all medication dispensing robotic devices may be provided higher weighted scores as opposed to other available robotic devices that do not have dispensing capabilities.

Once scores are determined, the system may compare the score for each of the capabilities to a best fit threshold to determine if the respective robotic device is capable of assisting a given user in performing a specific activity. Using the bipartite graph, if the score of the capability exceeds the best fit threshold, the system will draw an edge connecting the user node requiring a robotic device for a specific activity to a robotic device node with a score indicating the robotic device is capable of performing the specific activity. Using the bipartite graph, users may be matched with robotic devices that are capable of assisting the users in performing their given set of activities.

In embodiments, once the matching has been completed using the bipartite graph, the system will identify a first robotic device that is capable of assisting the one or more users in performing a first activity of the set of activities. For example, multiple robotic devices may have been matched and/or assigned to a user that requires assistance performing a given set of activities. For example, the user may require assistance getting out of bed in the morning, walking in the afternoon, and being lifted onto rehabilitation equipment in the evening. Using activity prediction, the bipartite graph, and/or machine learning, the system will identify a first robotic device that is available and capable of aiding the user when getting out of bed in the morning (e.g., the first activity). Once the first robotic device is identified for the first activity, the system will deploy the first robotic device at the predicted time point (e.g., average time user gets out of bed in the morning based on observation data) to provide the user with assistance.

In embodiments, the system may monitor the performance of the first robotic device when assisting the user with the first activity using the one or more observation devices. Using observation data, the system may determine that the first robotic device has successfully helped the user complete the first activity. For example, the first robotic device may be equipped with an onboard camera or voice recognition software that can detect either visually or through a user's voice confirmation that the first activity has been completed. For example, the system may determine the first robotic device has helped the user out of bed by analyzing observation data of the robotic device physically lifting the patient, thus completing the first activity. Once the first activity has been completed, the respective robotic device may be added back to the pool of available robotic devices ready for redeployment to assistance other users with their ongoing set of activities.

In embodiments, the system may determine if/when the user is ready to move onto another or next activity by utilizing a user feedback model. For example, while a robotic device is assisting a user in performing range of motion exercises, the system via an observation device (e.g., an onboard camera) may detect facial expressions indicating pain on the face of the user (e.g., emotion recognition) or through voice recognition that the user would like to move on to a different activity. Using the user feedback model during the activity, the system will identify that the user has completed the given activity and will move onto a next predicted activity.

In embodiments, the system may continuously match users with robotic devices using the bipartite graph/matching algorithm as each user completes a given activity of the set of activities. This allows the system to dynamically allocate robotic devices as needs change for each of the users. As the users move through their set of predicted activities, the system will dynamically match available robotic devices to the users ready for performing a next activity.

Returning to the previous example, now that the first user has completed their first activity (e.g., getting out of bed), the system will identify a second robotic device to assist the user in performing their second activity (e.g., walking in the afternoon). The system will determine which robotic device is capable of assisting the first user with walking and if the current robotic device is available to assist by reperforming matching using the bipartite graph. The system will determine current availability of the robotic devices by monitoring the workload of each of the robotic devices that have been deployed to each user and whether the respective activities requiring assistance have been completed. Once identified, the system will deploy the second robotic device to help the user complete their second activity, and so on, until all activities of the set of activities requiring assistance have been completed. In this way, the robotic devices are continuously matched with users to efficiently manage the time and effectiveness of the robotic devices with regard to assisting the users. In some embodiments, matching may occur on a scheduled interval or whenever a user wishes to change/complete their current activity.

In some embodiments, the system may utilize machine learning to analyze historic performance of the robotic devices when assisting users to determine which robotic devices have expediently and successfully helped the users complete various types of activities. Once determined, robotic devices with highest success rates may be implemented initially or more frequently by the system to improve the efficiency of the robotic devices in providing care. In this way, the system may become more accurate in providing appropriate/expedient care to users.

In embodiments, the user(s) must opt into the system in order for the system to collect their information, and the user may determine which other users (e.g., healthcare provider(s), physicians, physical therapist, etc.) can utilize the collected data. For example, during an initialization process, the system may inform the user of the types of data that it will collect (e.g., observation data, EHRs, etc.) and the reasons why the data is being collected. In these embodiments, the system will only start collecting the user's information/data upon the user explicitly permitting the collection. Furthermore, the system may only collect the data that is necessary to predict activities requiring robotic assistance and for assigning robotic devices to the user. The collected data may be anonymized and/or encrypted while in use, and the data may only be maintained as needed for assigning the robotic devices to the user. If the user chooses to opt out of the system, any user information previously collected may be permanently deleted.

The aforementioned advantages are example advantages, and not all advantages are discussed. Furthermore, embodiments of the present disclosure can exist that contain all, some, or none of the aforementioned advantages while remaining within the spirit and scope of the present disclosure.

With reference now to FIG. 1, shown is a block diagram of a robotic device assignment system 100, in accordance with embodiments of the present disclosure. In the illustrated embodiment, robotic device assignment system 100 includes robotic device scheduler 102 that is communicatively coupled to user device 120, observation device 130, historical data source 140 and robotic device 160 via network 150. Robotic device scheduler 102, user device 120, observation device 130, historical data source 140, and robotic device 160 may be configured as any type of computer system and may be substantially similar to computer system 1101 of FIG. 6. In embodiments, robotic device scheduler 102 may be a standalone computing device or virtual software application. For example, robotic device scheduler 102 may be a virtual application located on a server (not shown) that is accessed through a cloud computing network.

Network 150 may be any type of communication network, such as a wireless network or a cloud computing network. Network 150 may be substantially similar to, or the same as, cloud computing environment 50 described in FIG. 7. In some embodiments, network 150 can be implemented using any number of any suitable communications media. For example, the network may be a wide area network (WAN), a local area network (LAN), a personal area network (PAN), an internet, or an intranet. In certain embodiments, the various systems may be local to each other, and communicate via any appropriate local communication medium.

For example, robotic device scheduler 102 may communicate with user device 120, observation device 130, and robotic device 160 using a WAN, one or more hardwire connections (e.g., an Ethernet cable) and/or wireless communication networks. In some embodiments, the various systems may be communicatively coupled using a combination of one or more networks and/or one or more local connections. For example, robotic device scheduler 102 may communicate with observation device 130 using a hardwired connection, while communication between user device 120, robotic devices 160, and robotic device scheduler 102 may be through a wireless communication network.

User device 120 may be any type of device (e.g., smart phone, smart watch, computer, tablet, etc.) configured to communicate with robotic device scheduler 102. In embodiments, robotic device scheduler 102 may collect data from user device 120 to predict activities that may require assistance of robotic device 160. For example, robotic device scheduler 102 may access and analyze calendar information from a user's smartphone to identify various rehabilitation appointments for a specific impairment that may require robotic assistance (e.g., physical therapy appointments for rehabbing various extremities, medication schedule, etc.). In embodiments, robotic device scheduler 102 may communicate with user device 120 by sending notifications regarding assignment of robotic devices to accommodate various needs. For example, the robotic device scheduler 102 may send a schedule of assigned robotic devices for various activities to the user via user device 120 indicating the time, location, and type of assistance each robotic device will provide.

Observation device 130 may be any type of device (e.g., IoT camera, smart speaker, health monitor, smart watch, etc.) that is configured to observe a user performing various activities. Robotic device scheduler 102 may collect, monitor, and analyze observation data from multiple types observation devices 130 to determine and/or predict various activities that require the assistance of one or more robotic devices. For example, robotic device scheduler 102 may collect observation data from a set of IoT cameras that have been monitoring a user performing range of motion exercises for an extremity (e.g., arm, leg, hand) with the assistance of a physical therapist. In another example, robotic device scheduler 102 may collect biometric data from a health monitor indicating a user's blood pressure is elevated and image data of the user receiving blood pressure medication in response to the elevated blood pressure data. In this way, the robotic device scheduler 102 may determine various activities that may require the assistance of a robotic device (e.g., performing range of motion exercise, dispensing medication based on biometric data, etc.) by analyzing observation data generated by observation device 130.

Historical data source 140 may be any type of data source (e.g., EHR, medical records, physical therapy records, etc.) that can be collected and/or analyzed to assist in making predictions regarding activities. For example, robotic device scheduler 102 may collect EHR from historical data source 140 that is associated with a healthcare center where the user was treated and use that information to supplement the collected observation data. For example, robotic device scheduler 102 may determine that a user has a left-hand impairment by analyzing the user's EHR from historical data source 140. Using this information, the robotic device scheduler 102 can pinpoint various activities that the user may have difficulty performing based on the analysis of the EHR in conjunction with observation data and assign robotic device 160 to help perform those activities accordingly.

In the illustrated embodiment, robotic device scheduler 102 includes processor 104, activity prediction engine 106, user profile engine 108, machine learning engine 110, and database 112.

In embodiments, activity prediction engine 106 is configured analyze the observation data collected from observation device 130 and/or the information collected from historical data source 140 to determine and/or predict a set of activities to be performed by a user that require assistance from one or more robotic devices. Activity prediction engine 106 may use various recognition techniques (e.g., facial recognition, image recognition, natural language processing, etc.) to determine which activities a user is performing, and whether or not the user requires assistance of a robotic device 160. For example, the activity prediction engine 106 may analyze observation data generated by IoT cameras to determine that a user is being assisted by another user (e.g., a physical therapist) when performing range of motion exercises with the user's leg. Using recognition techniques, the activity prediction engine 106 may identify the type of activity the user is performing (e.g., range of motion exercises for the user's leg) and how the physical therapist is assisting the user (e.g., holding and/or moving the leg). The activity prediction engine 106 may use the observation data to predict that the user requires assistance from a robotic device 160 that is capable of assisting the user in performing the same range of motion exercises. The activity prediction engine 106 may analyze observation data generated from multiple types of observation devices 130 to determine/predict a set of activities for one or more users that require the assistance of one or more robotic devices.

User profile engine 108 is configured to generate a user profile for each respective user that is monitored by robotic device assignment system 100. For example, the user profile engine 108 may identify users using facial recognition algorithms when analyzing the observation data and generate a user profile. The user profile engine 108 may store user profiles on database 112 of robotic device scheduler 102 or on user device 120. The user profile engine 108 may store the predicted set of activities that require assistance of a robotic device with the user profile where the activities can be tracked and/or updated as each activity is completed by a given robotic device. Robotic device scheduler 102 may send notifications to users by identifying the user through their user profile. The user profile may include contact information for identify user devices 120 that associated with a respective user.

In embodiments, machine learning engine 110 may collect, monitor, and/or analyze data generated by the robotic device assignment system 100 to dynamically assign robotic devices to users based on specific needs. Machine learning engine 110 may match the users with robotic devices 160 that are capable of assisting the users in performing predicted activities by generating a bipartite graph as detailed in FIGS. 4-5B.

In embodiments, machine learning engine 110 may comprise various machine learning engines (artificial neural network, correlation engines, reinforcement feedback learning model, supervised/unsupervised learning model, etc.) configured to analyze data generated by robotic device assignment system 100 to improve predictions for assigning appropriate robotic devices to users in need. For example, machine learning engine 110 may analyze historic performance of each of the robotic devices when assisting users and determine which robotic devices have expediently and successfully helped the users complete various types of activities. Once determined, robotic devices with highest success rates may be implemented initially or more frequently by the system to improve the efficiency of the robotic devices in providing care. In this way, the system may become more accurate in providing appropriate and expedient care to users.

Machine learning algorithms can include, but are not limited to, decision tree learning, association rule learning, artificial neural networks, deep learning, inductive logic programming, support vector machines, clustering, Bayesian networks, reinforcement learning, representation learning, similarity/metric training, sparse dictionary learning, genetic algorithms, rule-based learning, and/or other machine learning techniques.

For example, the machine learning algorithms can utilize one or more of the following example techniques: K-nearest neighbor (KNN), learning vector quantization (LVQ), self-organizing map (SOM), logistic regression, ordinary least squares regression (OLSR), linear regression, stepwise regression, multivariate adaptive regression spline (MARS), ridge regression, least absolute shrinkage and selection operator (LASSO), elastic net, least-angle regression (LARS), probabilistic classifier, naïve Bayes classifier, binary classifier, linear classifier, hierarchical classifier, canonical correlation analysis (CCA), factor analysis, independent component analysis (ICA), linear discriminant analysis (LDA), multidimensional scaling (MDS), non-negative metric factorization (NMF), partial least squares regression (PLSR), principal component analysis (PCA), principal component regression (PCR), Sammon mapping, t-distributed stochastic neighbor embedding (t-SNE), bootstrap aggregating, ensemble averaging, gradient boosted decision tree (GBDT), gradient boosting machine (GBM), inductive bias algorithms, Q-learning, state-action-reward-state-action (SARSA), temporal difference (TD) learning, apriori algorithms, equivalence class transformation (ECLAT) algorithms, Gaussian process regression, gene expression programming, group method of data handling (GMDH), inductive logic programming, instance-based learning, logistic model trees, information fuzzy networks (IFN), hidden Markov models, Gaussian naïve Bayes, multinomial naïve Bayes, averaged one-dependence estimators (AODE), Bayesian network (BN), classification and regression tree (CART), chi-squared automatic interaction detection (CHAID), expectation-maximization algorithm, feed-forward neural networks, logic learning machine, self-organizing map, single-linkage clustering, fuzzy clustering, hierarchical clustering, Boltzmann machines, convolutional neural networks, recurrent neural networks, hierarchical temporal memory (HTM), and/or other machine learning techniques.

FIG. 1 is intended to depict the representative major components of robotic device assignment system 100. In some embodiments, however, individual components may have greater or lesser complexity than as represented in FIG. 1, components other than or in addition to those shown in FIG. 1 may be present, and the number, type, and configuration of such components may vary. Likewise, one or more components shown with robotic device assignment system 100 may not be present, and the arrangement of components may vary.

For example, while FIG. 1 illustrates an example robotic device assignment system 100 having a single robotic device scheduler 102, a single user device 120, a single observation device 130, a single historical data source 140, and a single robotic device 160, communicatively coupled via a single network 150, suitable network architectures for implementing embodiments of this disclosure may include any number of robotic device schedulers, user devices, observation devices, historical data sources, robotic devices, and networks. The various models, modules, systems, and components illustrated in FIG. 1 may exist, if at all, across a plurality of robotic device schedulers, user devices, observation devices, historical data sources, robotic devices, and networks.

Figure 2:
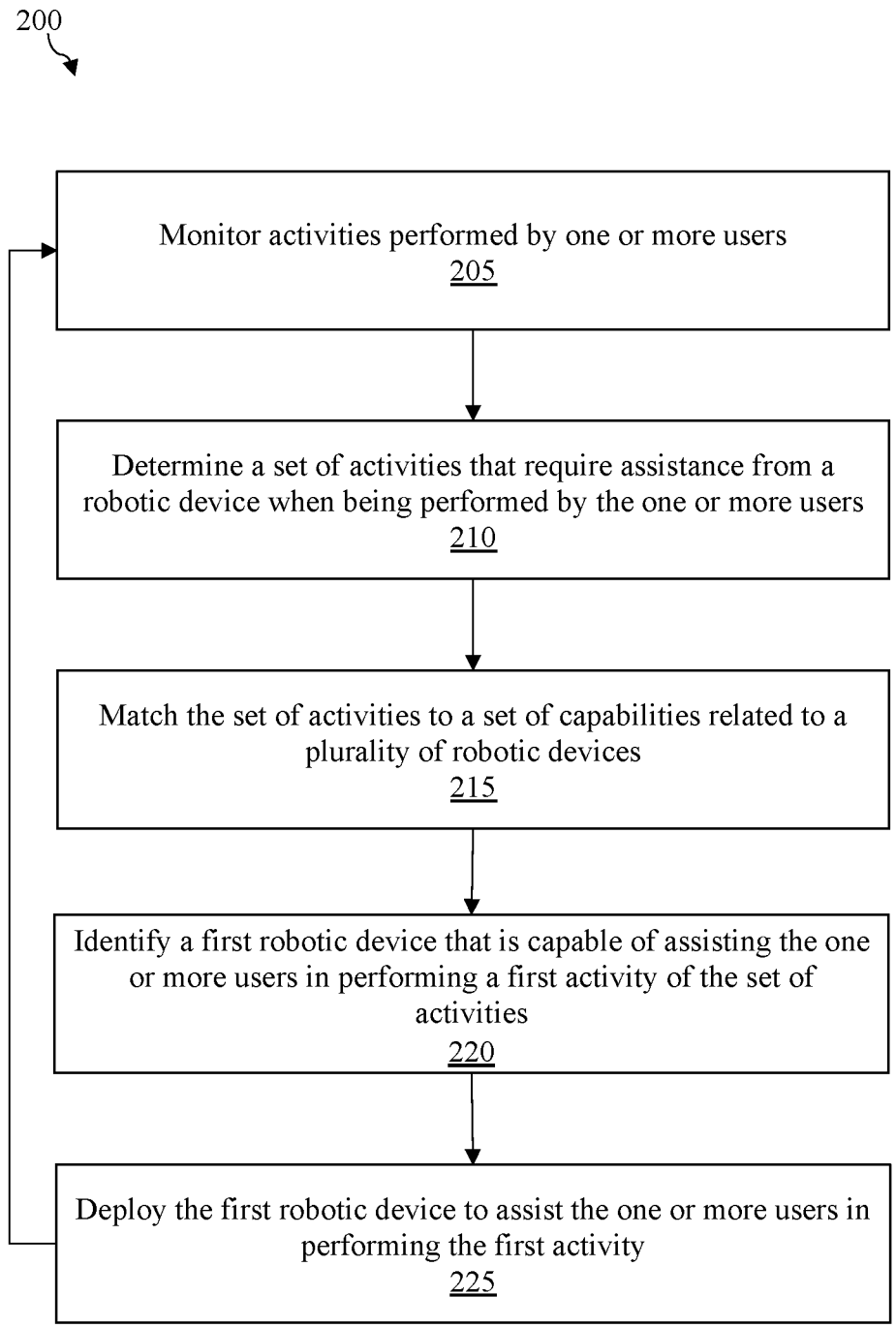
FIG. 2 illustrates a flow diagram of an example process for assigning a robotic device to one or more users, in accordance with embodiments of the present disclosure.

Referring now to FIG. 2, shown is a flow diagram of an example process 200 for assigning a robotic device to one or more users, in accordance with embodiments of the present disclosure. The process 200 may be performed by processing logic that comprises hardware (e.g., circuitry, dedicated logic, programmable logic, microcode, etc.), software (e.g., instructions run on a processor), firmware, or a combination thereof. In some embodiments, the process 200 is a computer-implemented process. The process 200 may be performed by processor 104 exemplified in FIG. 1.

The process 200 begins by monitoring activities performed by one or more users. This is illustrated at step 205. In embodiments, the system (e.g., robotic device assignment system 100 of FIG. 1) may monitor the one or more users performing various activities via one or more observation devices (e.g., biometric monitor/sensor, IoT camera, smart band, etc.). For example, the system may utilize a set of IoT cameras positioned within an environment (e.g., hospital, rehabilitation center, assisted living center, etc.) to generate observation data of a first user (e.g., patients, residents, etc.) performing various activities. For example, the system may monitor/observe the first user being assisted by a second user (e.g., caretaker, physical therapist, etc.) when getting out of bed in the morning, performing range of motion exercises in the afternoon, and taking medication at different time points throughout the day or when experiencing pain.

The process 200 continues by determining, based on the monitoring, a set of activities that require assistance from a robotic device when being performed by the one or more users. This is illustrated at step 210. Using the observation data, the system may determine and/or identify (e.g., via activity prediction engine 106 of FIG. 1) which activities may require the assistance of one or more robotic devices using known recognition techniques. Returning to the previous example, the system may determine that the first user requires assistance of a robotic device when getting out of bed, performing the range of motion exercises, and taking medication by identifying the presence of the second user helping the first user perform each activity by analyzing the observation data.

The system may observe these activities over multiple days and determine a pattern of activities performed by the one or more users. Using the observation data, the system can determine which activities may require assistance of a robotic device and when/where (e.g., time and location) the assistance is needed. In embodiments, the system may further analyze historical data that can be used to predict activities that require robotic assistance. For example, the system may analyze electronic health records to determine various ailments/impairments that affect activities perform by the one or more users which may require assistance of a robotic device.

The process 200 continues by matching the set of activities to a set of capabilities related to a plurality of robotic devices. This is illustrated at step 215. In embodiments, the system may access a database enumerating various capabilities related to multiple types of robotic devices. The system may provide a best fit score for each capability related to each available robotic device that is computed based on a suitability for performing a given activity required by the one or more users. For example, a first robotic device may include capabilities, such as a lifting capacity of 250 lbs. and the presence of robotic appendages that can assist a user in performing range of motion exercises, while a second robotic device may include medication dispensing capabilities and/or a pain recognition determination software (e.g., using facial recognition and/or health monitoring sensors). The system will score each capability and compare the score to a best fit threshold related to a specific activity required by the user.

Returning to the previous example, the first robotic device would be given a score that meets or exceeds the best fit threshold for helping the first user get out of bed if the user is under 250 lbs. because the first robotic device has a lifting capacity of 250 lbs. Further, the first robotic device would be given a score that meets the best fit threshold for performing range of motion exercises required by the first user based on the presence of the robotic appendages capable of assisting in those same exercises. However, the first robotic device would not meet the best fit threshold for providing medication because it does not include medication dispensing capabilities. Therefore, the second robotic device would be additionally assigned to the first user because it has a score that meets the best fit threshold for dispensing medication.

Figure 4:
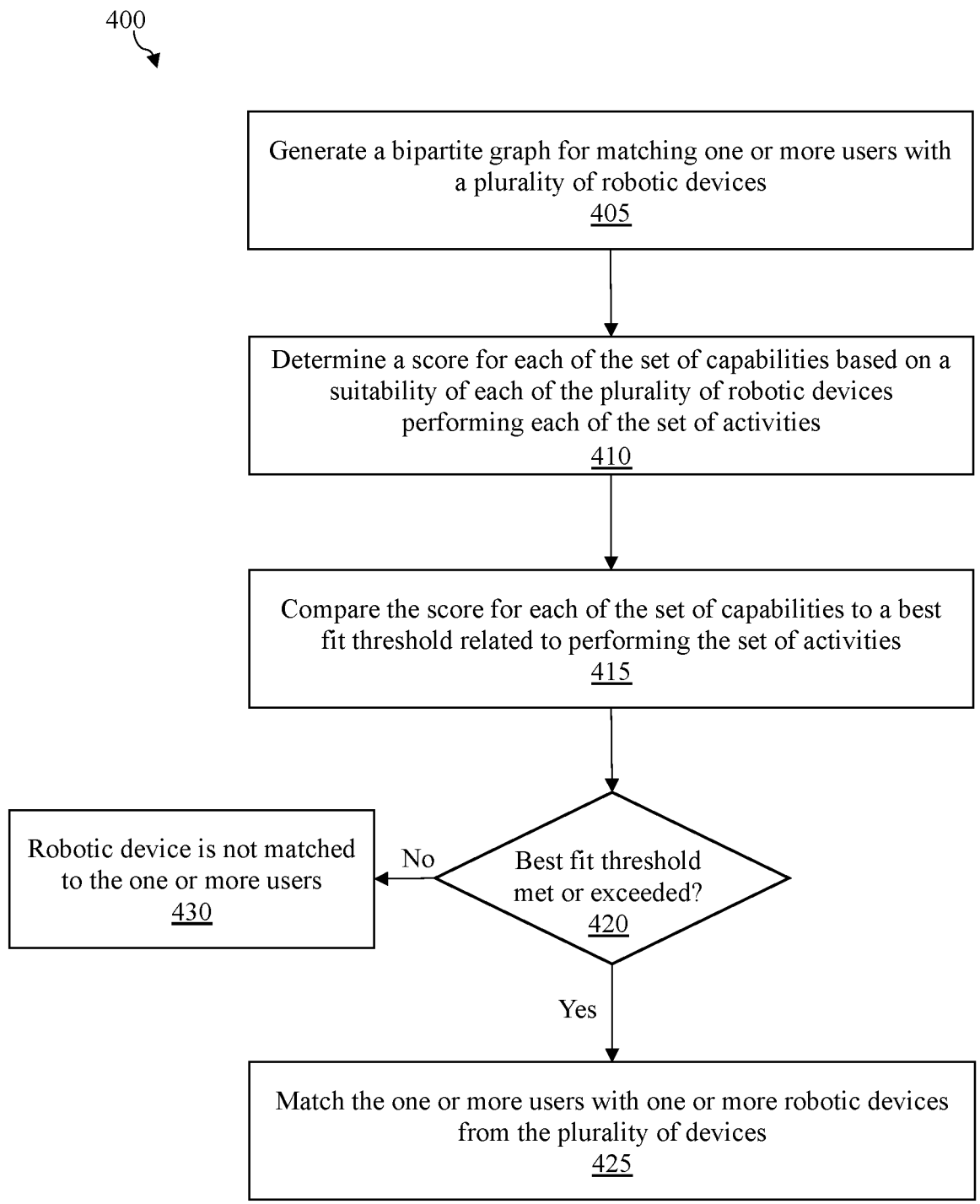
FIG. 4 illustrates a flow diagram of an example process for generating a bipartite graph for matching users to robotic devices, in accordance with embodiments of the present disclosure.
Figure 5A:
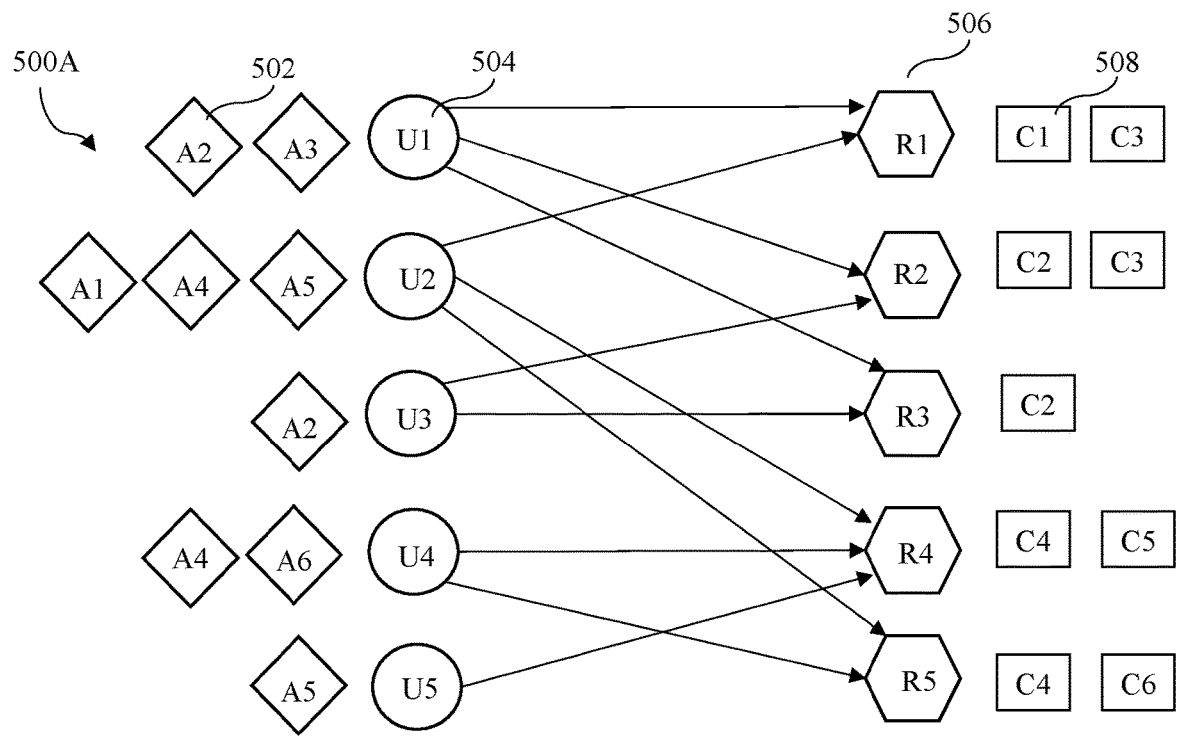
FIG. 5A illustrates an example bipartite graph for matching robotic devices to users, in accordance with embodiments of the present disclosure.
Figure 5B:
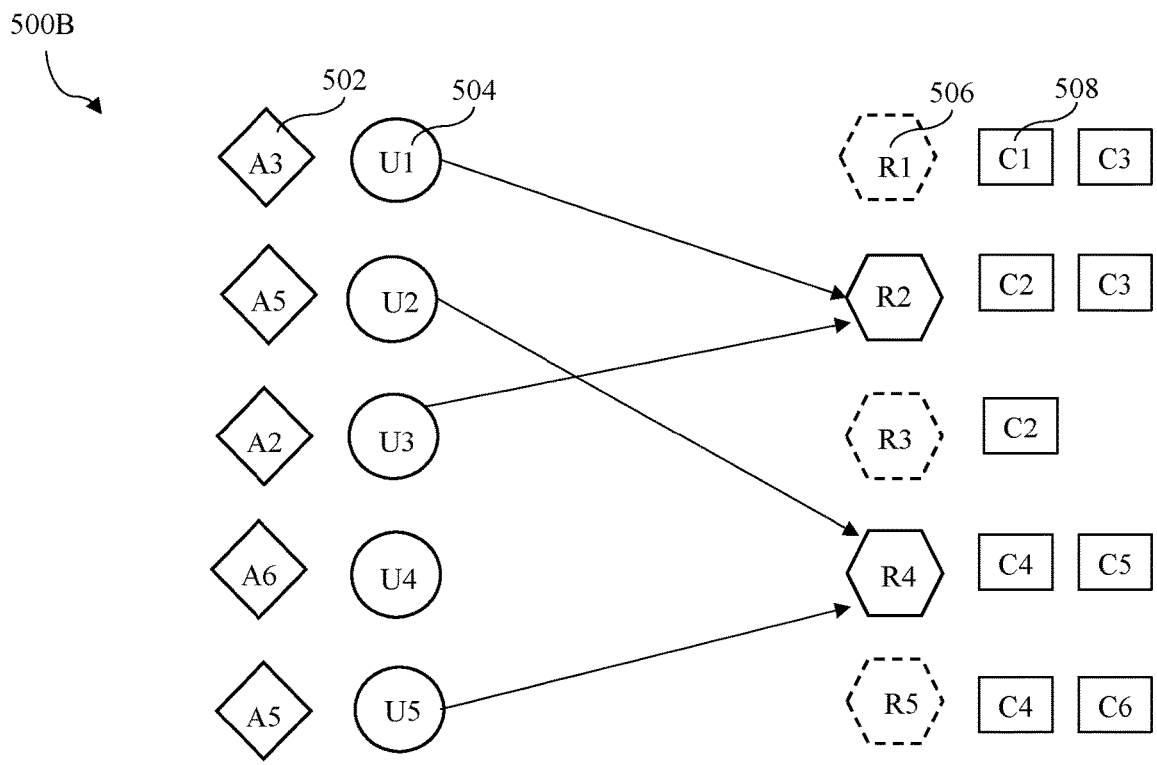
FIG. 5B illustrates an updated example bipartite graph in response to determining an activity has been completed, in accordance to embodiments of the present disclosure.

In embodiments, the system may match the set of activities related to the one or more users to the set of capabilities related to the robotic devices by utilizing a bipartite graph, which is described in more detail in FIG. 4, FIG. 5A, and FIG. 5B.

The process 200 continues by identifying, based on the matching, a first robotic device that is capable of assisting the one or more users in performing a first activity of the set of activities. This is illustrated at step 220. Once the system has determined which robotic devices are capable of assisting the user in performing their set of activities, the system will identify which robotic device would be needed for the first activity based on what activity is predicted to be performed by the user at each given time point. Returning to the previous example, the system will identify the first robotic device is capable of assisting the first user with getting out of bed in the morning (e.g., the first activity in the user's set of activities). Once the first robotic device is identified, the process 200 continues by deploying the first robotic device to assist the one or more users in performing the first activity. This is illustrated at step 225. In embodiments, the first robotic device will be deployed at the appropriate time schedule to assist the user in performing the first activity based on the predicted set of activities from step 210. Once the first activity has been completed, the system will deploy subsequent robotic devices to aid the user in completing the rest of their given set of activities which is detailed in FIG. 3.

In embodiments, the system may return to step 205 to continuously monitor the activities performed by the one or more users to determine if any new activities have been implemented by the user that may require the assistance of a robotic device. For example, over time the needs of a user may change, and various activities will be added to their daily routine, such as new rehabilitation exercises, social interaction routines, and/or updated medication schedules. In the way, the system continuously monitors the user's routine to determine new activities requiring assistance and automatically allocates appropriate robotic devices that are capable of assisting the user based on need.

Figure 3:
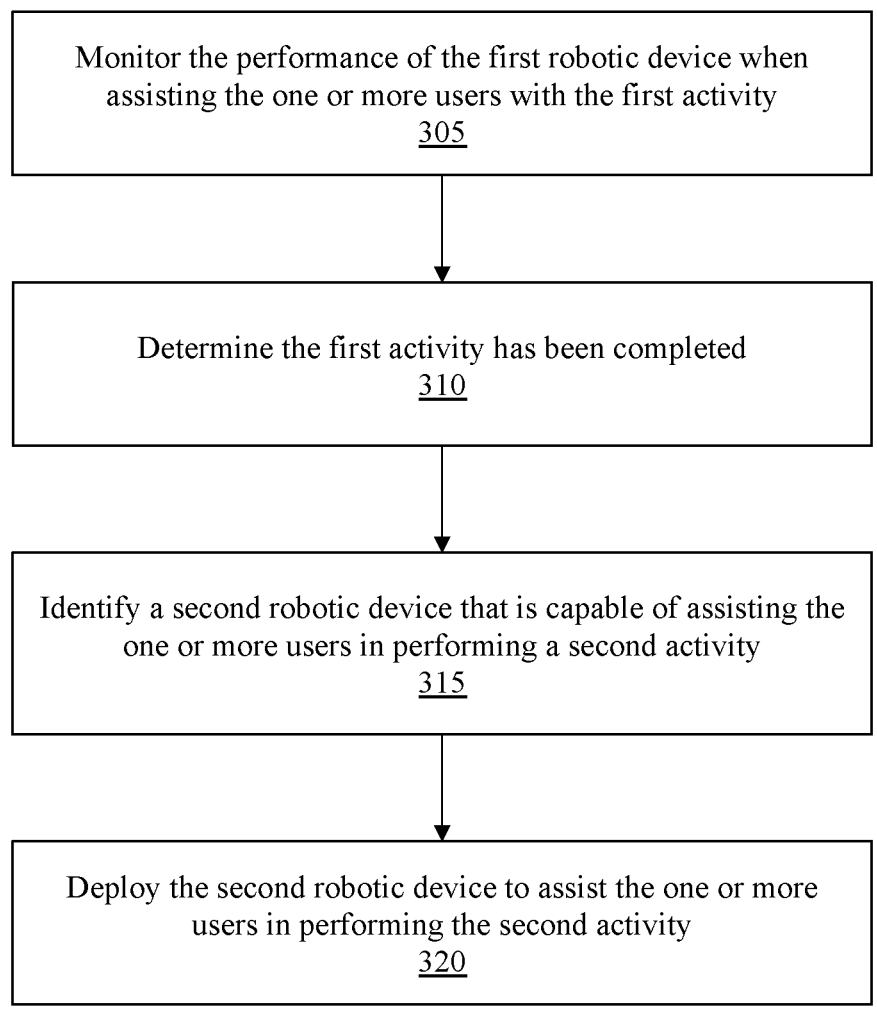
FIG. 3 illustrates a flow diagram of an example process for deploying a subsequent robotic device in response to completion of an activity, in accordance with embodiments of the present disclosure.

Referring now to FIG. 3, shown is a flow diagram of an example process 300 for deploying a subsequent robotic device in response to completion of an activity, in accordance with embodiments of the present disclosure. The process 300 may be performed by processing logic that comprises hardware (e.g., circuitry, dedicated logic, programmable logic, microcode, etc.), software (e.g., instructions run on a processor), firmware, or a combination thereof. In embodiments, process 300 may be, in addition to, or a subset of process 200. In embodiments, the process 300 is a computer-implemented process. The process 300 may be performed by processor 104 exemplified in FIG. 1.

The process 300 begins by monitoring the performance of the first robotic device when assisting the one or more users with the first activity. This is illustrated at step 305. In embodiments, the monitoring may be performed using one or more observation devices (e.g., IoT cameras, sensors, health monitors, question and answer (Q&A) system, etc.). For example, the first robotic device may include an onboard camera that can monitor the first robotic device's performance when assisting a user with the first activity. In another example, the performance of the first robotic device may be monitored by responses given by the user to an onboard Q&A system of the first robotic device.

The process 300 continues by determining the first activity has been completed. This is illustrated at step 310. The system may determine the first activity has been completed by using the various observation devices. For example, if the first activity is to lift the user out of a bed, the system may determine the first activity has been completed by analyzing image data from an on-board camera disposed on the first robotic device indicating the user is completely out of the bed. In another example, if the first activity is helping the user walk, the system may determine the first activity is completed based on image data of the user sitting or via responses given to the Q&A system of the first robotic device by the user indicating the user is finished walking.

In embodiments, the system may use various known approaches (e.g., visual cues, voice, facial emotion detection) to infer the user's response to an activity that is underway, and if the response is unfavorable, the system will identify that the activity is complete and will move on to a next/second activity. For example, if the first robotic device is aiding the user in performing rehabilitation exercises as the first activity, the system may identify the user is experiencing significant pain based on facial emotion detection and determine that the user is ready to move on to a next activity.

Once the system has determined that the first activity has been completed, the process 300 continues by identifying, based on the matching and a current availability of the plurality of robotic devices, a second robotic device that is capable of assisting the one or more users in performing a second activity of the set of activities. This is illustrated at step 315. In embodiments, the matching of the set of activities to the set of capabilities related to the plurality of robotic devices is continuously performed when one of the set of activities for the one or more users has been completed. In this way, the system may continuously allocate available robot devices to assist users that are moving on to their next activities.

For example, the system will allocate any available robotic device that has a capability score meeting the best fit threshold for a given activity. If no robotic devices are currently available, the system may implement a wait time for the next available robotic device and notify the user of the wait time. The availability of the robotic devices may be monitored/determined based on the workload for each robotic device. For example, the system may predict how long various activities may take for each user to complete and determine the workload of all the robotic devices based on this prediction. In embodiments, if the system determines that significant wait times for the robotic devices repeatedly occur, the system may recommend to a master user (e.g., system administrator, manual scheduler, etc.) that more robotic devices are needed to meet the demand.

The process 300 continues by deploying the second robotic device to assist the one or more users in performing the second activity. This is illustrated at step 320. Once deployed, the system will monitor the performance of the second robotic device when assisting the one or more users with the second activity and determine when the second activity has been completed. Once the second activity is completed, the system will continue to identify and deploy subsequent robotic devices for assisting the users in completing the remaining set of activities.

Referring now to FIG. 4, shown is a flow diagram of an example process 400 for generating a bipartite graph for matching users to robotic devices, in accordance with embodiments of the present disclosure. The process 400 may be performed by processing logic that comprises hardware (e.g., circuitry, dedicated logic, programmable logic, microcode, etc.), software (e.g., instructions run on a processor), firmware, or a combination thereof. In embodiments, process 400 may be, in addition to, or a subset of process 200 or 300. In some embodiments, the process 400 is a computer-implemented process. The process 400 may be performed by processor 104 exemplified in FIG. 1.

The process 400 begins by generating a bipartite graph for matching one or more users with a plurality of robotic devices. This is illustrated at step 405. In embodiments, the system may utilize a machine learning engine to generate the bipartite graph. The matching may be performed by the system on a scheduled interval (e.g., each morning, different time points in a day, weekly, etc.) or autonomously as users complete various activities. The bipartite graph includes a set of user nodes and a plurality of robotic device nodes that are available for matching. Each user node is associated with a set of activities that require assistance from a robotic device. While each robotic device node includes a set of capabilities related to performing various activities. An example of a bipartite graph is detailed in FIGS. 5A and 5B.

The process 400 continues by determining a score for each capability of the set of capabilities based on a suitability of each robotic device of the plurality of robotic devices performing each activity of the set of activities. This is illustrated at step 410. The system may use any type of scoring model to determine the score for each capability (e.g., range from 0 to 1, 0 to 100, percentage, etc.). For example, a first robotic device may include capabilities for socially interacting with users (e.g., reading, talking, singing, etc.) and be provided a score of 1 for capabilities related to reading to a user, while receiving a score of 0 for capabilities related to assisting a user with taking medications. While a second robotic device may include capabilities for dispensing medication and given a score of 1 for providing medication to a user while receiving a score of 0 for social interactions.

The process 400 continues by comparing the score for each of the set of capabilities to a best fit threshold related to performing the set of activities. This is illustrated at step 415. The score for each capability will be compared to a best fit threshold related to performing each activity required by the user. The best fit threshold may be any type of threshold (e.g., minimum, maximum, range, etc.). If the score for a given capability of a robotic device does not meet a best fit threshold ("No" at step 420) for a specific activity, the process 400 will continue by not matching a given robotic device the one or more users because it is not capable of performing the activity. This is illustrated step 430. Returning to the previous example, the system will compare the scores of the capabilities of the first robotic device for best fit thresholds for both of the activities of reading and medication dispensing. Because the first robotic device received a 0 for medication dispensing capabilities it would not be matched with the user for that given activity.

If the score meets or exceeds the best fit threshold ("Yes" at step 420), the process 400 will continue by matching the one or more users with one or more robotic devices from the plurality of devices. This is illustrated at step 425. For example, because the first robotic device was given a score of 1 for reading capabilities, it would meet or exceed the best fit threshold for the reading activity related to the user's set of activities requiring assistance. Using the bipartite graph, the system will draw an edge from (e.g., recognize a connection between) users to robotic devices that include capabilities that meet or exceed best fit thresholds related to the given activity. In embodiments, the system may utilize standard maximum bipartite matching to obtain optimal matching for users to robotic devices based on each of the robotic device's capabilities.

Referring now to FIG. 5A and FIG. 5B, shown is an example bipartite graph 500A for matching robotic devices to users and an updated example bipartite graph 500B in response to determining an activity has been completed, respectively, in accordance with embodiments of the present disclosure. In the illustrated embodiments, bipartite graph 500A and 500B each include a plurality of user nodes 504 (U1-U5) that are associated with a set of activities 502 (A1-A6) requiring assistance from at least one robotic device to complete. Further, the bipartite graphs 500A and 500B include a plurality of robotic device nodes 506 (R1-R5) that include a set of capabilities 508 (C1-C6) related to a suitability for performing the various activities 502. In embodiments, each of the capabilities 508 are scored by the system based on whether the respective robotic device is suitable for performing the given activity 502. The score is then compared to a best fit threshold to determine if the robotic device is a suitable match for assisting the user in performing a given activity. If the score meets the best fit threshold, edges are drawn from the user node 504 to the robotic device node 506 that is capable of performing the given activity 502.

For example, in FIG. 5A the first user node U1 requires a robotic device that is capable of providing assistance for activities A2 and A3. Because robotic device nodes R2 and R3 are capable of performing at least one of activities A2 and A3 (based on having capabilities C2 and/or C3), they are matched with user node U1. Bipartite graph 500A depicts an initial matching scheme of robotic device nodes to user nodes based on availability. As robotic devices are deployed to assist users with various activities, the pool of available robotic devices may decrease as shown in bipartite graph 500B. For example, initially both robotic devices R2 and R3 were matched with user U1 in bipartite graph 500A, but because matching occurs dynamically as other users may require assistance from robotic devices, only robotic device R2 is available to user U1 when the user is ready to move on to the next activity as shown in bipartite graph 500B. In this way, the system will continuously match users with available robotic devices that are capable of performing the given activity.

Figure 6:
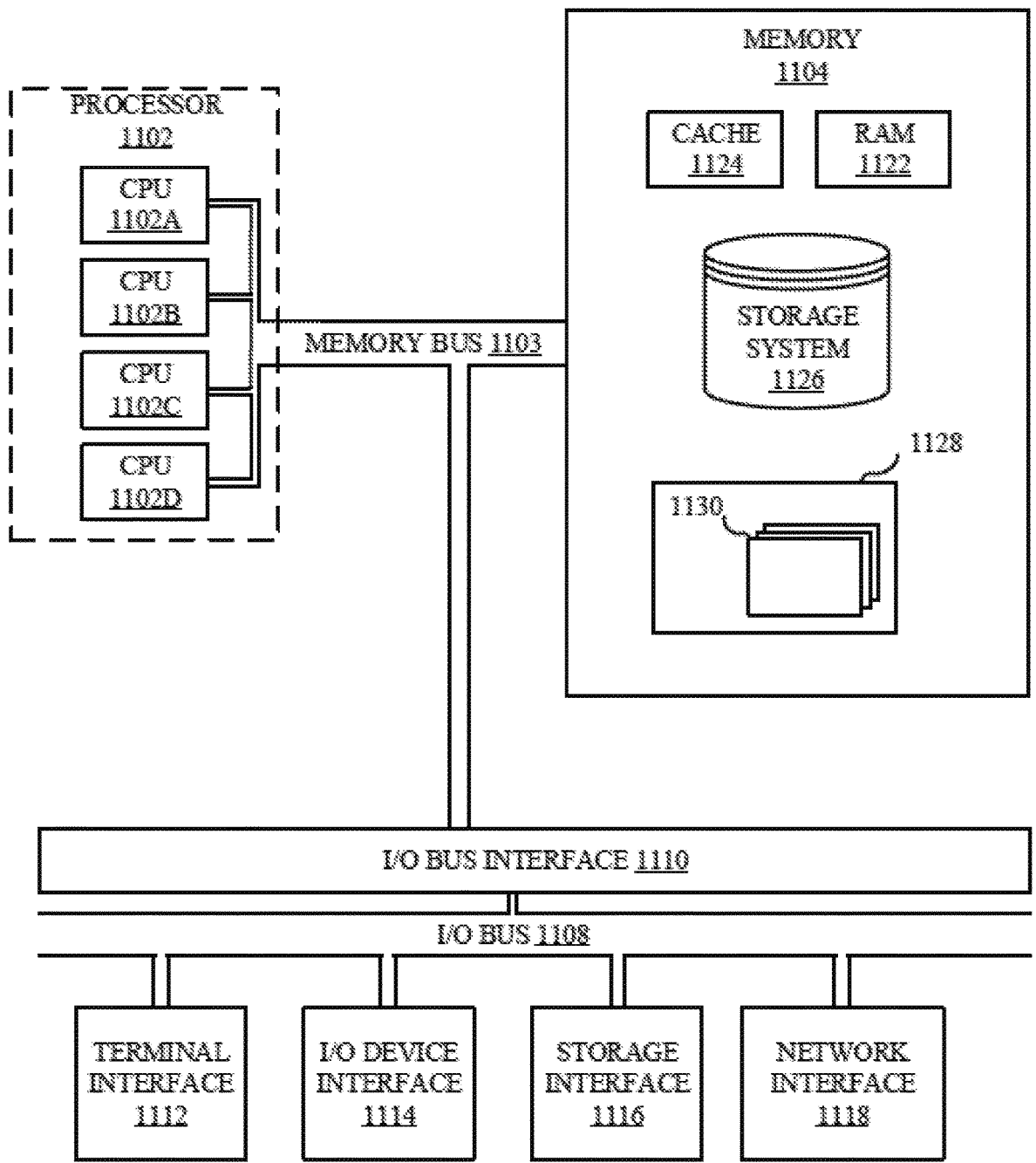
FIG. 6 illustrates a high-level block diagram of an example computer system that may be used in implementing one or more of the methods, tools, and modules, and any related functions, described herein, in accordance with embodiments of the present disclosure.

Referring now to FIG. 6, shown is a high-level block diagram of an example computer system 1101 that may be used in implementing one or more of the methods, tools, and modules, and any related functions, described herein (e.g., using one or more processor circuits or computer processors of the computer), in accordance with embodiments of the present disclosure. In some embodiments, the major components of the computer system 1101 may comprise one or more CPUs 1102, a memory subsystem 1104, a terminal interface 1112, a storage interface 1116, an I/O (Input/Output) device interface 1114, and a network interface 1118, all of which may be communicatively coupled, directly or indirectly, for inter-component communication via a memory bus 1103, an I/O bus 1108, and an I/O bus interface 1110.

The computer system 1101 may contain one or more general-purpose programmable central processing units (CPUs) 1102A, 1102B, 1102C, and 1102D, herein generically referred to as the CPU 1102. In some embodiments, the computer system 1101 may contain multiple processors typical of a relatively large system; however, in other embodiments the computer system 1101 may alternatively be a single CPU system. Each CPU 1102 may execute instructions stored in the memory subsystem 1104 and may include one or more levels of on-board cache. In some embodiments, a processor can include at least one or more of, a memory controller, and/or storage controller. In some embodiments, the CPU can execute the processes included herein (e.g., process 200, 300, and 400).

System memory subsystem 1104 may include computer system readable media in the form of volatile memory, such as random-access memory (RAM) 1122 or cache memory 1124. Computer system 1101 may further include other removable/non-removable, volatile/non-volatile computer system data storage media. By way of example only, storage system 1126 can be provided for reading from and writing to a non-removable, non-volatile magnetic media, such as a "hard drive." Although not shown, a magnetic disk drive for reading from and writing to a removable, non-volatile magnetic disk (e.g., a "floppy disk"), or an optical disk drive for reading from or writing to a removable, non-volatile optical disc such as a CD-ROM, DVD-ROM or other optical media can be provided. In addition, memory subsystem 1104 can include flash memory, e.g., a flash memory stick drive or a flash drive. Memory devices can be connected to memory bus 1103 by one or more data media interfaces. The memory subsystem 1104 may include at least one program product having a set (e.g., at least one) of program modules that are configured to carry out the functions of various embodiments.

Although the memory bus 1103 is shown in FIG. 6 as a single bus structure providing a direct communication path among the CPUs 1102, the memory subsystem 1104, and the I/O bus interface 1110, the memory bus 1103 may, in some embodiments, include multiple different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface 1110 and the I/O bus 1108 are shown as single units, the computer system 1101 may, in some embodiments, contain multiple I/O bus interfaces 1110, multiple I/O buses 1108, or both. Further, while multiple I/O interface units are shown, which separate the I/O bus 1108 from various communications paths running to the various I/O devices, in other embodiments some or all of the I/O devices may be connected directly to one or more system I/O buses.

In some embodiments, the computer system 1101 may be a multi-user mainframe computer system, a single-user system, or a server computer or similar device that has little or no direct user interface, but receives requests from other computer systems (clients). Further, in some embodiments, the computer system 1101 may be implemented as a desktop computer, portable computer, laptop or notebook computer, tablet computer, pocket computer, telephone, smart phone, network switches or routers, or any other appropriate type of electronic device.

It is noted that FIG. 6 is intended to depict the representative major components of an exemplary computer system 1101. In some embodiments, however, individual components may have greater or lesser complexity than as represented in FIG. 6, components other than or in addition to those shown in FIG. 6 may be present, and the number, type, and configuration of such components may vary.

One or more programs/utilities 1128, each having at least one set of program modules 1130 may be stored in memory subsystem 1104. The programs/utilities 1128 may include a hypervisor (also referred to as a virtual machine monitor), one or more operating systems, one or more application programs, other program modules, and program data. Each of the operating systems, one or more application programs, other program modules, and program data or some combination thereof, may include an implementation of a networking environment. Programs/utilities 1128 and/or program modules 1130 generally perform the functions or methodologies of various embodiments.

It is understood in advance that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 7:
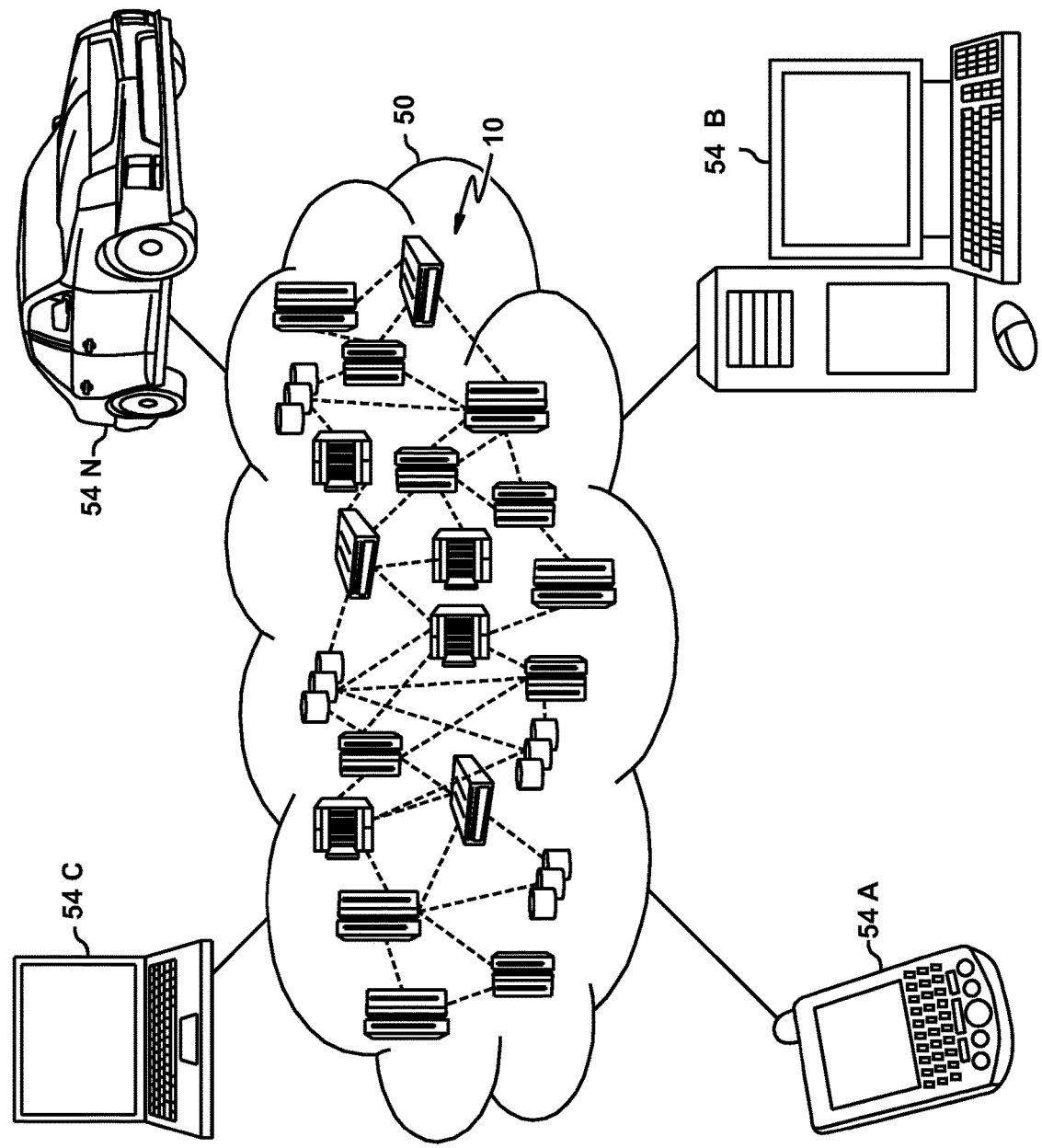
FIG. 7 depicts a cloud computing environment in accordance with embodiments of the present disclosure.

Referring now to FIG. 7, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 7 are intended to be illustrative only and that computing nodes 10 and cloud computing environment 50 can communicate with any type of computerized device over any type of network and/or network addressable connection (e.g., using a web browser).

Figure 8:
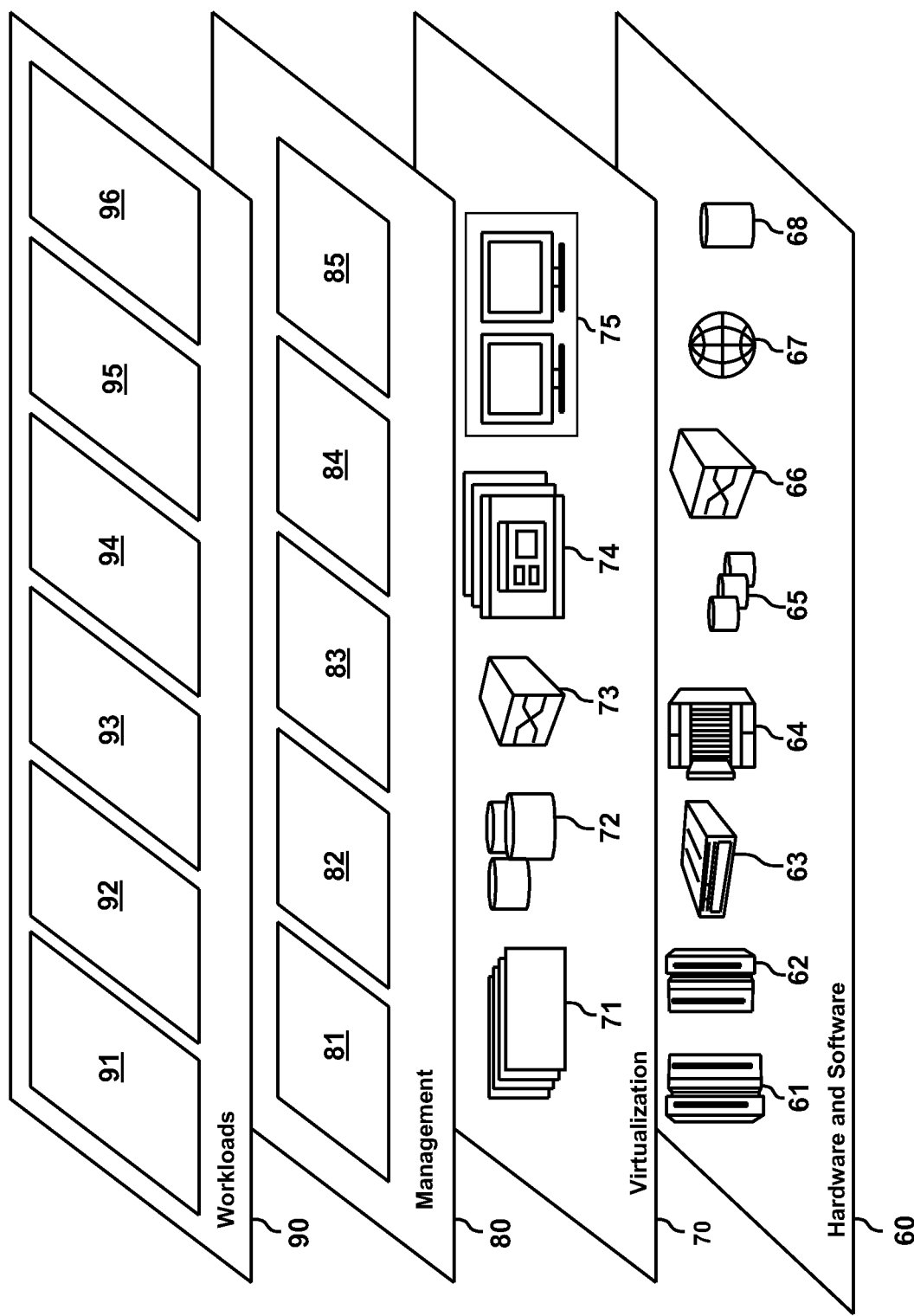
FIG. 8 depicts abstraction model layers in accordance with embodiments of the present disclosure.

Referring now to FIG. 8, a set of functional abstraction layers provided by cloud computing environment 50 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and robotic device scheduling software 68 in relation to the robotic device scheduler 102 of FIG. 1.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and mobile desktops 96.

As discussed in more detail herein, it is contemplated that some or all of the operations of some of the embodiments of methods described herein may be performed in alternative orders or may not be performed at all; furthermore, multiple operations may occur at the same time or as an internal part of a larger process.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the various embodiments. As used herein, the singular forms "a," "an," and "the" are intended to include the plural forms as well, unless the context clearly indicates otherwise. It will be further understood that the terms "includes" and/or "including," when used in this specification, specify the presence of the stated features, integers, steps, operations, elements, and/or components, but do not preclude the presence or addition of one or more other features, integers, steps, operations, elements, components, and/or groups thereof. In the previous detailed description of example embodiments of the various embodiments, reference was made to the accompanying drawings (where like numbers represent like elements), which form a part hereof, and in which is shown by way of illustration specific example embodiments in which the various embodiments may be practiced. These embodiments were described in sufficient detail to enable those skilled in the art to practice the embodiments, but other embodiments may be used and logical, mechanical, electrical, and other changes may be made without departing from the scope of the various embodiments. In the previous description, numerous specific details were set forth to provide a thorough understanding the various embodiments. But, the various embodiments may be practiced without these specific details. In other instances, well-known circuits, structures, and techniques have not been shown in detail in order not to obscure embodiments.

As used herein, "a number of" when used with reference to items, means one or more items. For example, "a number of different types of networks" is one or more different types of networks.

When different reference numbers comprise a common number followed by differing letters (e.g., 100*a*, 100*b*, 100*c*) or punctuation followed by differing numbers (e.g., 100-1, 100-2, or 100.1, 100.2), use of the reference character only without the letter or following numbers (e.g., 100) may refer to the group of elements as a whole, any subset of the group, or an example specimen of the group.

Further, the phrase "at least one of," when used with a list of items, means different combinations of one or more of the listed items can be used, and only one of each item in the list may be needed. In other words, "at least one of" means any combination of items and number of items may be used from the list, but not all of the items in the list are required. The item can be a particular object, a thing, or a category.

For example, without limitation, "at least one of item A, item B, or item C" may include item A, item A and item B, or item B. This example also may include item A, item B, and item C or item B and item C. Of course, any combinations of these items can be present. In some illustrative examples, "at least one of" can be, for example, without limitation, two of item A; one of item B; and ten of item C; four of item B and seven of item C; or other suitable combinations.

Different instances of the word "embodiment" as used within this specification do not necessarily refer to the same embodiment, but they may. Any data and data structures illustrated or described herein are examples only, and in other embodiments, different amounts of data, types of data, fields, numbers and types of fields, field names, numbers and types of rows, records, entries, or organizations of data may be used. In addition, any data may be combined with logic, so that a separate data structure may not be necessary. The previous detailed description is, therefore, not to be taken in a limiting sense.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Although the present invention has been described in terms of specific embodiments, it is anticipated that alterations and modification thereof will become apparent to the skilled in the art. Therefore, it is intended that the following claims be interpreted as covering all such alterations and modifications as fall within the true spirit and scope of the invention.

What is claimed is:

1. A computer-implemented method comprising:
   monitoring activities performed by one or more users;
   determining, based on the monitoring, a set of activities that require assistance from a robotic device when being performed by the one or more users;

matching the set of activities to a set of capabilities related to a plurality of robotic devices, wherein the matching comprises:
generating a bipartite graph for matching the one or more users with the plurality of robotic devices;
determining a score for each of the set of capabilities based on a suitability of each of the plurality of robotic devices performing each of the set of activities;
comparing the score for each of the set of capabilities to a best fit threshold related to performing each of the set of activities; and
matching, using the bipartite graph, the one or more users with one or more robotic devices from the plurality of devices if the score for each of the set of capabilities exceeds the best fit threshold;
identifying, based on the matching, a first robotic device that is capable of assisting the one or more users in performing a first activity of the set of activities; and
deploying the first robotic device to assist the one or more users in performing the first activity.

2. The computer-implemented method of claim 1, wherein matching the set of activities to the set of capabilities related to the plurality of robotic devices is continuously performed when one of the set of activities has been completed.

3. The computer-implemented method of claim 1, the method further comprising:
monitoring a performance of the first robotic device when assisting the one or more users with the first activity;
determining the first activity has been completed;
identifying, based on the matching and a current availability of the plurality of robotic devices, a second robotic device that is capable of assisting the one or more users in performing a second activity of the set of activities; and
deploying the second robotic device to assist the one or more users in performing the second activity.

4. The computer-implemented method of claim 3, wherein the current availability is determined by monitoring a workload of each of the plurality of robotic devices.

5. The computer-implemented method of claim 3, wherein determining the first activity has been completed utilizes a user feedback model.

6. The computer-implemented method of claim 1, wherein monitoring the activities performed by the one or more users is done by one or more observation devices.

7. The computer-implemented method of claim 6, wherein the one or more observation devices are selected from a group consisting of: a wearable health monitor; an Internet of Things (IoT) camera; a smart watch; a smart sensor; and a smart speaker.

8. The computer-implemented method of claim 1, wherein determining the set of activities includes analyzing historical data records related to the one or more users.

9. The computer-implemented method of claim 8, wherein the historical data records are electronic health records.

10. A system comprising:
a processor; and
a computer-readable storage medium communicatively coupled to the processor and storing program instructions which, when executed by the processor, cause the processor to perform a method comprising:
monitoring activities performed by one or more users;
determining, based on the monitoring, a set of activities that require assistance from a robotic device when being performed by the one or more users;
matching the set of activities to a set of capabilities related to a plurality of robotic devices, wherein the matching comprises:
generating a bipartite graph for matching the one or more users with the plurality of robotic devices;
determining a score for each of the set of capabilities based on a suitability of each of the plurality of robotic devices performing each of the set of activities;
comparing the score for each of the set of capabilities to a best fit threshold related to performing each of the set of activities; and
matching, using the bipartite graph, the one or more users with one or more robotic devices from the plurality of devices if the score for each of the set of capabilities exceeds the best fit threshold;
identifying, based on the matching, a first robotic device that is capable of assisting the one or more users in performing a first activity of the set of activities; and
deploying the first robotic device to assist the one or more users in performing the first activity.

11. The system of claim 10, wherein matching the set of activities to the set of capabilities related to the plurality of robotic devices is continuously performed when one of the set of activities has been completed.

12. The system of claim 10, wherein the method performed by the processor further comprises:
monitoring a performance of the first robotic device when assisting the one or more users with the first activity;
determining the first activity has been completed;
identifying, based on the matching and a current availability of the plurality of robotic devices, a second robotic device that is capable of assisting the one or more users in performing a second activity of the set of activities; and
deploying the second robotic device to assist the one or more users in performing the second activity.

13. The system of claim 12, wherein the current availability is determined by monitoring a workload of each of the plurality of robotic devices.

14. A computer program product comprising a computer-readable storage medium having program instructions embodied therewith, the program instructions executable by a processor to cause the processor to perform a method comprising:
monitoring activities performed by one or more users;
determining, based on the monitoring, a set of activities that require assistance from a robotic device when being performed by the one or more users;
matching the set of activities to a set of capabilities related to a plurality of robotic devices, wherein the matching comprises:
generating a bipartite graph for matching the one or more users with the plurality of robotic devices;
determining a score for each of the set of capabilities based on a suitability of each of the plurality of robotic devices performing each of the set of activities;
comparing the score for each of the set of capabilities to a best fit threshold related to performing each of the set of activities; and
matching, using the bipartite graph, the one or more users with one or more robotic devices from the plurality of devices if the score for each of the set of capabilities exceeds the best fit threshold;

identifying, based on the matching, a first robotic device that is capable of assisting the one or more users in performing a first activity of the set of activities; and deploying the first robotic device to assist the one or more users in performing the first activity.

15. The computer program product of claim 14, wherein matching the set of activities to the set of capabilities related to the plurality of robotic devices is continuously performed when one of the set of activities has been completed.

16. The computer program product of claim 14, wherein the method performed by the processor further comprises:

monitoring a performance of the first robotic device when assisting the one or more users with the first activity;

determining the first activity has been completed;

identifying, based on the matching and a current availability of the plurality of robotic devices, a second robotic device that is capable of assisting the one or more users in performing a second activity of the set of activities; and deploying the second robotic device to assist the one or more users in performing the second activity.

17. The computer program product of claim 16, wherein the current availability is determined by monitoring a workload of each of the plurality of robotic devices.

* * * * *